United States Patent
Hayakawa

(10) Patent No.: US 11,607,470 B2
(45) Date of Patent: Mar. 21, 2023

(54) METHOD AND APPARATUS FOR STERILIZING STERILIZATION FILTER UNIT

(71) Applicant: Dai Nippon Printing Co., Ltd., Tokyo (JP)

(72) Inventor: Atsushi Hayakawa, Tokyo (JP)

(73) Assignee: Dai Nippon Printing Co., Ltd., Tokyo (JP)

( * ) Notice: Subject to any disclaimer, the term of this patent is extended or adjusted under 35 U.S.C. 154(b) by 283 days.

(21) Appl. No.: 16/762,990

(22) PCT Filed: Dec. 6, 2018

(86) PCT No.: PCT/JP2018/044878
§ 371 (c)(1),
(2) Date: May 11, 2020

(87) PCT Pub. No.: WO2019/111994
PCT Pub. Date: Jun. 13, 2019

(65) Prior Publication Data
US 2020/0268917 A1    Aug. 27, 2020

(30) Foreign Application Priority Data

Dec. 8, 2017   (JP) .............................. JP2017-236009

(51) Int. Cl.
*A61L 2/20* (2006.01)
*A61L 2/07* (2006.01)

(52) U.S. Cl.
CPC .................. *A61L 2/07* (2013.01); *A61L 2/208* (2013.01); *A61L 2202/14* (2013.01); *A61L 2202/15* (2013.01); *A61L 2202/23* (2013.01)

(58) Field of Classification Search
CPC .................................................. A61L 2209/14
See application file for complete search history.

(56) References Cited

U.S. PATENT DOCUMENTS

| | | | |
|---|---|---|---|
| 2014/0348700 | A1 | 11/2014 | Foreman et al. |
| 2015/0291406 | A1 | 10/2015 | Hayakawa et al. |
| 2016/0121376 | A1 | 5/2016 | Hayakawa et al. |

FOREIGN PATENT DOCUMENTS

| | | |
|---|---|---|
| CN | 105246821 A | 1/2016 |
| CN | 205972052 U | 2/2017 |
| JP | S57-093061 A1 | 6/1982 |

(Continued)

OTHER PUBLICATIONS

Translation of WO2014103787, 2014.*

(Continued)

*Primary Examiner* — Kevin Joyner
*Assistant Examiner* — Changru Chen
(74) *Attorney, Agent, or Firm* — Burr Patent Law, PLLC

(57) ABSTRACT

To sterilize a sterilization filter unit with heated steam, minimize the heat load on the sterilization filter unit and extend the service life of the sterilization filter unit.
Heated steam is supplied to a sterilization filter unit that sterilizes supplied air, the temperature of the heated steam discharged from the sterilization filter unit is measured at predetermined time intervals, the F value is calculated from the measured temperature, and sterilization of the sterilization filter unit is ended when the F value reaches a target value.

4 Claims, 4 Drawing Sheets

(56) References Cited

FOREIGN PATENT DOCUMENTS

| | | |
|---|---|---|
| JP | H10-016925 A1 | 1/1998 |
| JP | 2000-197882 A1 | 7/2000 |
| JP | 2015-006920 A1 | 1/2015 |
| JP | 2015-006921 A1 | 1/2015 |
| JP | 2015-084795 A1 | 5/2015 |
| JP | 2015-217366 A1 | 12/2015 |
| JP | 2016-523598 A1 | 8/2016 |
| JP | 2017-042309 A1 | 3/2017 |
| WO | 2014/103787 A1 | 7/2014 |
| WO | WO-2019164072 A1 * | 8/2019 ............. A61L 9/205 |

OTHER PUBLICATIONS

WO 2019164072 A1 Translation, 2019.*
International Search Report and Written Opinion (Application No. PCT/JP2018/044878) dated Feb. 5, 2019.

* cited by examiner

METHOD AND APPARATUS FOR STERILIZING STERILIZATION FILTER UNIT

FIELD OF THE INVENTION

The present invention relates to a method and an apparatus for sterilizing a sterilization filter unit that removes bacteria or the like in air used in an aseptic filling machine.

BACKGROUND OF THE INVENTION

An aseptic filling machine that aseptically fills a bottle with a drink or the like uses compressed aseptic air for various purposes, such as removal of foreign matters from a preform fed, spraying of a sterilizer used for sterilizing the preform, removal of the sterilizer, blow molding of the preform into a bottle, blasting of aseptic air to the sterilized preform to keep the preform aseptic while the preform is being conveyed, spraying of a sterilizer used for sterilizing the bottle, removal of the sterilizer and shooting of a cap when feeding the cap. Air piping through which the compressed aseptic air is supplied and a sterilization filter unit that removes bacteria or the like have to be sterilized before operation of the aseptic filling machine.

The piping for the compressed aseptic air and the sterilization filter unit are typically sterilized by heated steam. However, the steam sterilization has a problem that the service life of the sterilization filter unit decreases, and a method of sterilizing the sterilization filter unit with hydrogen peroxide has been proposed (Patent Literatures 1 and 2). Patent Literature 1 discloses that a hydrogen peroxide solution is sprayed and then heated for gasification, and the resulting hydrogen peroxide gas is fed to a sterilization filter unit. Patent Literature 2 discloses that hydrogen peroxide is supplied into air piping, and the hydrogen peroxide deposited in the piping is evaporated and fed to a filter by heated air. In both the methods, the sterilization filter unit is sterilized by gasified hydrogen peroxide. In short, for sterilizing the sterilization filter unit, there are methods of using heated steam and methods of using gasified hydrogen peroxide.

Drink supply piping of an aseptic filling machine is typically sterilized by hot water or steam. To prevent excessive sterilization, introducing F value management has been proposed. For example, it has been proposed that, when sterilizing by heating with hot water or steam the drink supply piping for feeding a drink from a drink heating and sterilization portion into the filling machine, the temperature of the drink supply piping is measured at a plurality of locations at predetermined time intervals to calculate the F value at the locations, and the sterilization process is ended when the minimum of the F values reaches a target value (Patent Literature 3).

It has also been proposed that, when feeding hot water or steam into the drink supply piping that feeds a drink to filling nozzles to sterilize the inside of the filling nozzles with the hot water or steam ejected from the filling nozzles, the temperature of the inside of all the filling nozzles is detected at predetermined time intervals to calculate the F value for the filling nozzles, and the sterilization process is ended when the minimum of the F values reaches a target value (Patent Literature 4).

CITATION LIST

Patent Literature

Patent Literature 1: Japanese Patent Laid-Open No. 10-16925

Patent Literature 2: Japanese Patent Laid-Open No. 2017-42309

Patent Literature 3: International Publication No. WO2014-103787

Patent Literature 4: Japanese Patent Laid-Open No. 2015-6920

SUMMARY OF THE INVENTION

Technical Problem

A sterilization filter unit that sterilize compresses air is sterilized with heated steam or gasified hydrogen peroxide. However, there is a problem that the sterilization filter unit has various parts made of resin, such as a support for a filter material, the filter material, an O-ring, and an end cap, and the resin deteriorates because of the heat of the heated steam and the gasified hydrogen peroxide, so that the service life of the sterilization filter unit is shortened.

Hydrogen peroxide has a problem that hydrogen peroxide is adsorbed by the resin forming the sterilization filter unit and remains therein, so that heated steam is preferably used for sterilization. However, when the heated steam is used for sterilization of the sterilization filter unit, the heat load on the resin forming the sterilization filter unit is high, and the resin can deteriorate. To avoid this, there is a demand for a method and an apparatus for sterilizing a sterilization filter unit that minimize the heat load on the sterilization filter unit and extend the service life of the sterilization filter unit.

An object of the present invention is to provide a method and an apparatus for sterilizing a sterilization filter unit that can solve the problems described above.

Solution to Problem

In a method for sterilizing a sterilization filter unit according to the present invention, heated steam is supplied to the sterilization filter unit, which sterilizes supplied air, a temperature of the heated steam discharged from the sterilization filter unit is measured at predetermined time intervals, an F value is calculated from the measured temperature, and sterilization of the sterilization filter unit is ended when the F value reaches a target value.

In the method for sterilizing a sterilization filter unit according to the present invention, the F value is preferably calculated according to the following formula:

$$F = \int_{t_0}^{t_1} 10^{(T-Tr)/Z} dt$$

wherein T is an optional sterilizing temperature (° C.), $10^{(T-Tr)/Z}$ is a fatality rate at the optional temperature T, Tr is a reference temperature (° C.), and Z is a Z value (° C.).

In the method for sterilizing a sterilization filter unit according to the present invention, the supplied air is preferably air having a pressure equal to or higher than 0.01 MPa.

In the method for sterilizing a sterilization filter unit according to the present invention, the air is preferably supplied to the sterilization filter unit after dust, oil or moisture is removed from the air.

In an apparatus for sterilizing a sterilization filter unit according to the present invention, a heated steam supply device is provided between an air supply apparatus and the sterilization filter unit, which sterilizes air supplied from the air supply apparatus, heated steam is supplied to the sterilization filter unit from the heated steam supply device, a temperature sensor is provided which measures a temperature of the heated steam discharged from the sterilization filter unit, the temperature of the discharged heated steam is measured at predetermined time intervals, a calculation apparatus is provided which calculates an F value from the measured temperature, and sterilization of the sterilization filter unit is ended when the F value reaches a target value.

Advantageous Effects of Invention

According to the present invention, in an aseptic filling machine, when sterilizing a sterilization filter unit that sterilizes compressed air used for removal of foreign matters from a preform fed, spraying of a sterilizer for sterilizing the preform, removal of the sterilizer, blow molding of the preform into a bottle, blasting of aseptic air to the sterilized preform to maintain the aseptic condition of the preform during conveyance thereof, spraying of a sterilizer for sterilizing the bottle, removal of the sterilizer, and shooting of a cap when feeding the cap, for example, heated steam used for the sterilization is managed through F-value control. Therefore, it is no longer required to unnecessarily raise the temperature of the heated steam or to unnecessarily extend the time for which the heated steam is supplied to the sterilization filter unit, so that the sterilization time can be reduced, the heat load on the sterilization filter unit can be reduced, and the service life of the sterilization filter unit can be extended.

DETAILED DESCRIPTION OF THE INVENTION

In the following, an embodiment of the present invention will be described with reference to the drawings.

Figure 1:
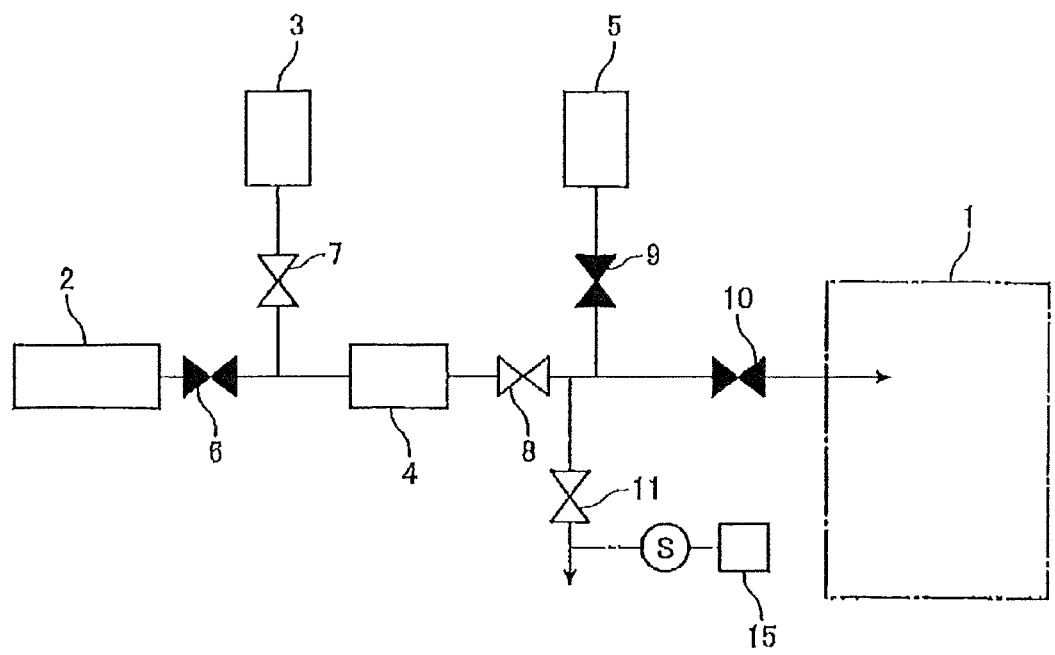
FIG. 1 a circuit diagram showing a configuration for sterilizing a sterilization filter unit according to an embodiment of the present invention.

In an aseptic filling machine, an aseptic chamber 1 houses a sterilizing machine that sterilizes a container to be sterilized, such as a bottle, a washing apparatus that washes the sterilized container, a filling apparatus that fills the washed container with a sterilized content, a sterilizing apparatus for a lid member that seals the container filled with the content, a sealing apparatus that seals the container with the sterilized lid member and a discharge apparatus that discharges the sealed container to the outside of the aseptic filling machine, for example, and air is supplied into the aseptic chamber 1 from an air supply apparatus 2 through air supply piping, as shown in FIG. 1.

The air supplied from the air supply apparatus 2 to the aseptic chamber 1 is sterilized by a sterilization filter unit 4 removing bacteria or the like from the air. When the aseptic filling machine is out of service, the aseptic chamber 1 is opened and therefore contaminated with bacteria or the like. The air in the aseptic chamber 1 thus contaminated can flow back through the air supply piping and contaminate the components downstream of the sterilization filter unit 4. Besides, the sterilization filter unit 4 is replaced after being used for a predetermined length of time, and the surface of a new replacement sterilization filter unit 4 is contaminated with bacteria or the like.

Therefore, when the aseptic filling machine is restarted after being stopped or after replacement of the sterilization filter unit 4, the sterilization filter unit 4 has to be sterilized. In addition, the part of the inside of the air supply piping from the sterilization filter unit 4 to the aseptic chamber 1 has to also be sterilized.

Figure 2:
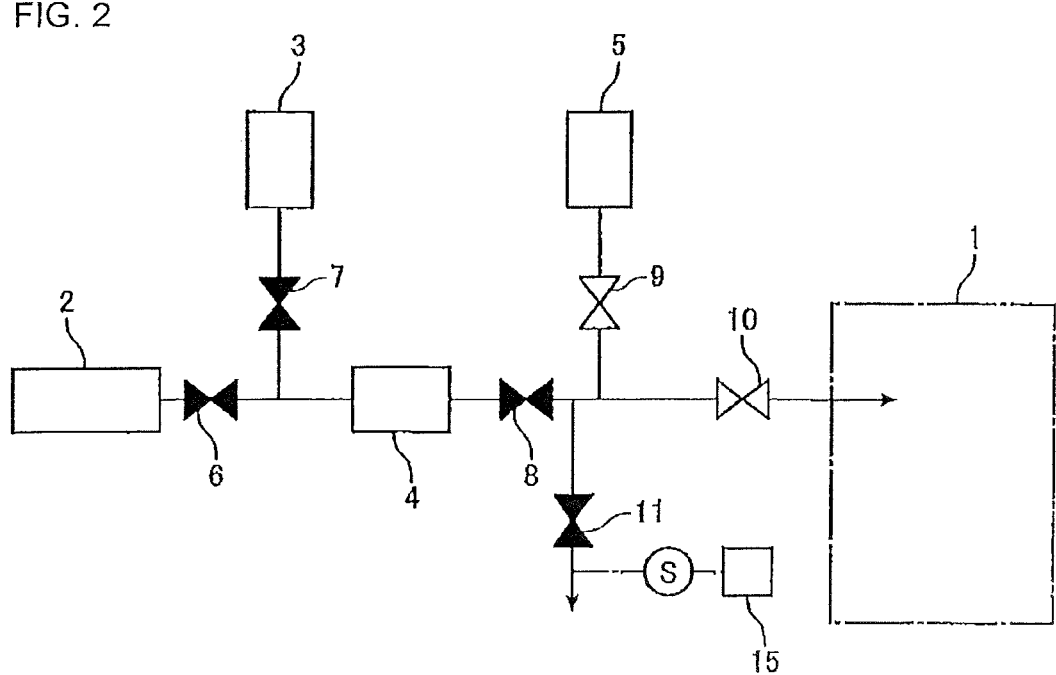
FIG. 2 is a circuit diagram showing a configuration for sterilizing air supply piping for supplying air to an aseptic filling machine according to the embodiment of the present invention.
Figure 3:
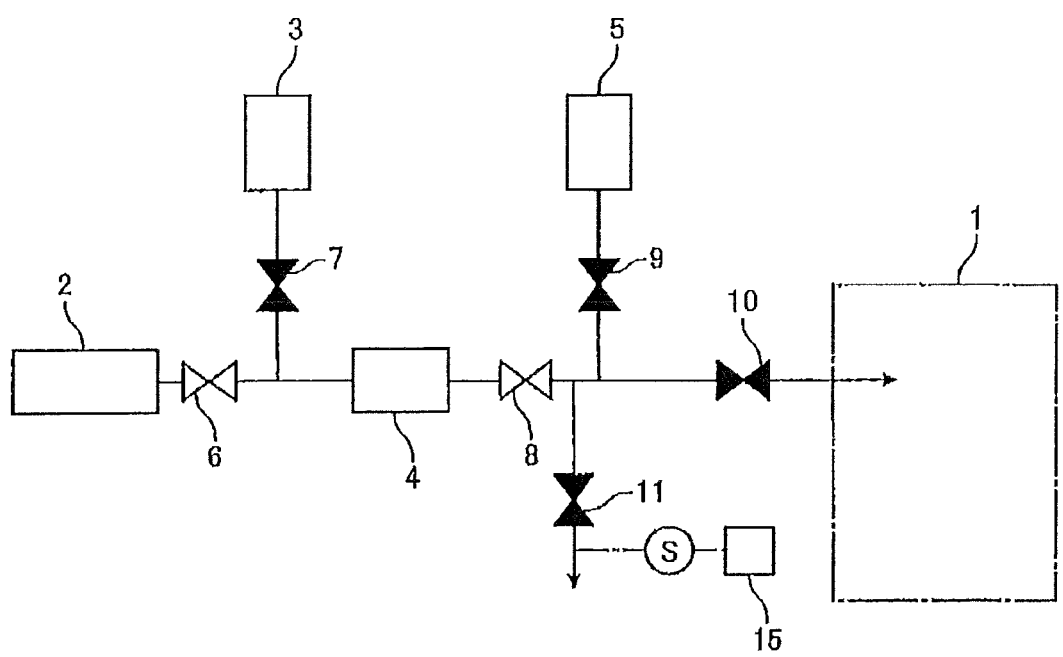
FIG. 3 is a circuit diagram showing a configuration during operation of the aseptic filling machine according to the embodiment of the present invention.

FIG. 1 is a circuit diagram showing a configuration for sterilizing the sterilization filter unit 4. An on-off valve 6 connected to the air supply apparatus 2 is closed, and heated steam is supplied to the sterilization filter unit 4 from a heated steam supply device 3, which is provided between the air supply apparatus 2 and the sterilization filter unit 4 that sterilizes the air supplied from the air supply apparatus 2. In this step, on-off valves 7, 8 and 11 are open. The heated steam supplied from the heated steam supply device 3 is supplied to the sterilization filter unit 4 and discharged through the on-off valve 11. In FIGS. 1, 2 and 3, the on-off valves colored black are closed, and the on-off valves colored white are open.

A temperature sensor S is provided at a location downstream of the sterilization filter unit 4 and downstream of the on-off valve 11. When the heated steam is supplied to the sterilization filter unit 4, the temperature of the discharged heated steam is measured by the temperature sensor S at predetermined time intervals, the resulting temperature measurement information is transmitted to a controller 15, and the controller 15, which includes a calculation apparatus that calculates the F value, calculates the F value. When the F value reaches a target value, the supply of the heated steam from the heated steam supply device 3 is stopped in response to a signal from the controller 15, and the sterilization of the sterilization filter unit 4 is ended.

The F value is determined from the temperature measured by the temperature sensor S and transmitted to the controller 15 according to the following formula.

$$F = \int_{t_0}^{t_1} 10^{(T-Tr)/Z} dt$$

wherein T is an optional sterilizing temperature (° C.), $10^{(T-Tr)/Z}$ is a fatality rate at the optional temperature T, Tr is a reference temperature (° C.), and Z is a Z value (° C.).

Provided that Tr in the formula is 121.1° C., when the temperature measured by the temperature sensor S reaches 121.1° C., the calculation apparatus in the controller 15 starts calculating the F value. The Z value for spore fungus to be killed is 7° C. to 11° C. For example, the calculation can be performed on the assumption that the Z value is 10° C. The Z value and the target F value can be arbitrarily set to the level of sterilization required for the content to be charged by the aseptic filling machine.

When the pH of the content is equal to or more than 4 and less than 4.6, the reference temperature Tr can be set at 85° C., and the Z value can be set at 7.8° C. When the pH of the content is less than 4, the reference temperature Tr can be set at 65° C., and the Z value can be set at 5° C., although the values can be changed as required. When the pH is equal to or more than 4.6, the calculation can be performed on the assumption that the reference temperature Tr is 121.1° C. and the Z value is 10° C.

Figure 4:
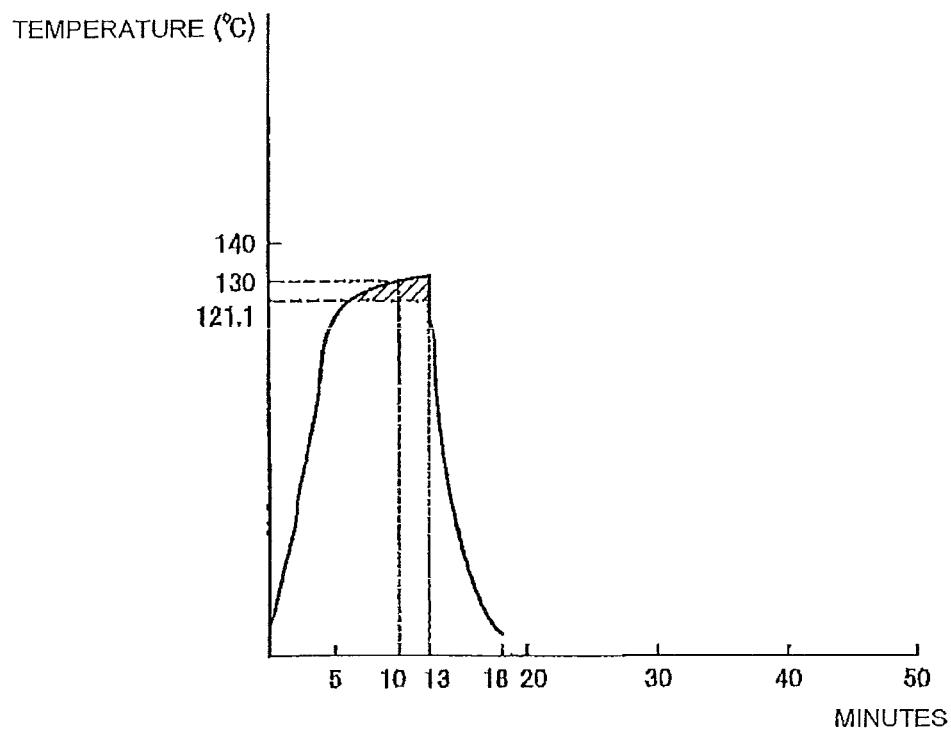
FIG. 4 is a graph showing a relationship between the temperature of heated steam and the sterilization time in sterilization of the sterilization filter unit according to the embodiment of the present invention.
Figure 5:
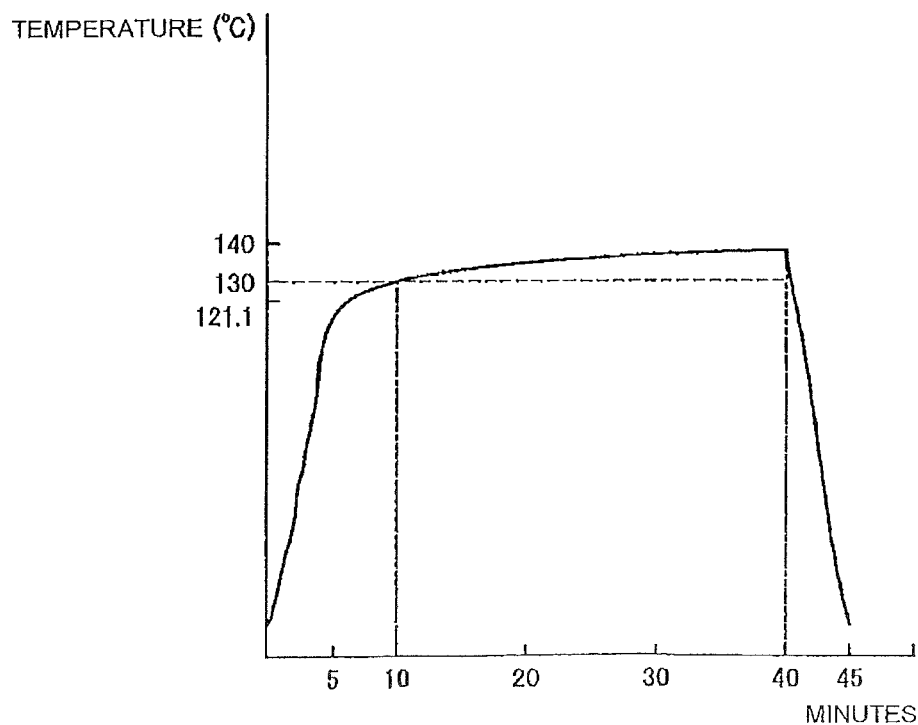
FIG. 5 is a graph showing a relationship between the temperature of heated steam and the sterilization time in conventional sterilization of the sterilization filter.

As shown in FIG. 4, the calculation of the F value starts when the temperature measured by the temperature sensor S reaches 121.1° C., and the sterilization ends when the F value, which is calculated from the temperature measured by the temperature sensor S and is represented by the area of the hatched part, reaches a target value. FIG. 5 shows an example of conventional art, in which a timer starts 10 minutes after the start of supply of the heated steam when the temperature measured by the temperature sensor S provided on the heated steam discharge pipe reaches 130° C., the sterilization ends 30 minutes after the start of the timer, and then the sterilization filter unit 4 is cooled over 5 minutes. That is, it takes approximately 45 minutes to sterilize the sterilization filter unit 4 from the start of the sterilization to the end of the cooling. In FIG. 4, since the sterilization time is managed based on the F value, it takes 5 minutes for the temperature to rise to 121.1° C., it takes 8 minutes for the F value to reach an $F_0=233$ (which is equivalent to the effect of the sterilization performed at 130° C. for 30 minutes), and it takes about 5 minutes to cool the sterilization filter unit 4. That is, the total time until the end of the cooling is 18 minutes, which is about 60% shorter, in terms of the time required for sterilizing the sterilization filter unit 4, than 45 minutes, which is the total time in the case of conventional art.

In addition to the time required to sterilize the sterilization filter unit 4, the time for which the sterilization filter unit 4 is exposed to the heated steam can also be reduced, and the temperature of the heated steam to which the sterilization filter unit 4 is exposed can also be reduced. As a result, the deterioration of the support member for the filter material, the filter material, the O-ring, the end cap and the like of the sterilization filter unit 4 can be reduced, and the service life of the sterilization filter unit 4 can be extended.

The heated steam supply device 3 heats water into steam by the heat from electricity or fuel, and the water used may be purified through a reverse osmosis membrane. A storage water heater body for changing water into steam is exposed to a boiler compound, a condensate treatment agent or the like, and the food additive grade is used for these agents. The storage water heater body and conveyance piping are preferably made of stainless steel. The heated steam may be passed through a filter, activated carbon, or an ultrafilter to remove foreign matters, ions, chemicals or the like from the heated steam. Furthermore, the heated steam supply device 3 is preferably a reboiler that produces heated steam through heat exchange between water passed through a reverse osmosis membrane and heated steam as a heat source.

The temperature of the heated steam supplied to the sterilization filter unit 4 is 121.1° C. to 150° C. A temperature lower than 121.1° C. is too low for sterilizing, and a temperature higher than 150° C. can cause deterioration of the members of the sterilization filter unit 4.

The sterilization filter unit 4 has a hollow cylindrical shape. A hollow cylindrical filter is housed in a removable housing and attached to the housing in such a manner that the filter can be inserted into the housing. The housing has an air inlet port through which air can be supplied into the hollow cylindrical filter unit from outside and a discharge port through which air having passed through a hollow portion of the hollow cylindrical filter unit is discharged. The housing has a drain reservoir at a lower part thereof, and an automatic drain trap that is in communication with the drain reservoir is attached to the housing.

The filter of the sterilization filter unit 4 can remove bacteria, mold, spore or the like. The filter has pores having a diameter of approximately 0.1 µm to 0.5 µm and is made of regenerated cellulose, nitrocellulose, or polytetrafluoroethylene, for example. The sterilization filter unit 4 is formed by placing such a filter having pores between support members that are non-woven fabric of polypropylene or cellulose, folding the resulting stack into a hollow shape, reinforcing the inside and outside of the resulting hollow body with mesh-like support cores made of stainless steel, and closing the top and bottom ends of the hollow body with end caps made of a heat resistant plastic material, such as polyphenylsulfone. The discharge port for discharging air from the hollow portion is formed in one of the end caps, and the discharge port of the housing is fixed to the piping via an O-ring made of silicon rubber or the like.

After the heated steam starts being supplied to the sterilization filter unit 4, when the F value calculated from the temperature measured by the temperature sensor S reaches a target value, the sterilization of the sterilization filter unit 4 is ended, and as shown in FIG. 2, the on-off valves 7, 8 and 11 are closed, the on-off valves 9 and 10 are opened to sterilize the part of the inside of the air supply piping from the on-off valve 8 located downstream from the sterilization filter unit 4 to the aseptic chamber 1. If this part is also sterilized with the heated steam, the time for which the sterilization filter unit 4 is exposed to the heated steam is extended to cause deterioration of the members of the sterilization filter unit 4. For this reason, the sterilization with the heated steam is used only for limited parts of the apparatus for sterilizing the sterilization filter unit 4. The part of the inside of the air supply piping from the on-off valve 8 to the aseptic chamber 1 is sterilized with a sterilizer, such as hydrogen peroxide or peracetic acid.

Figure 6:
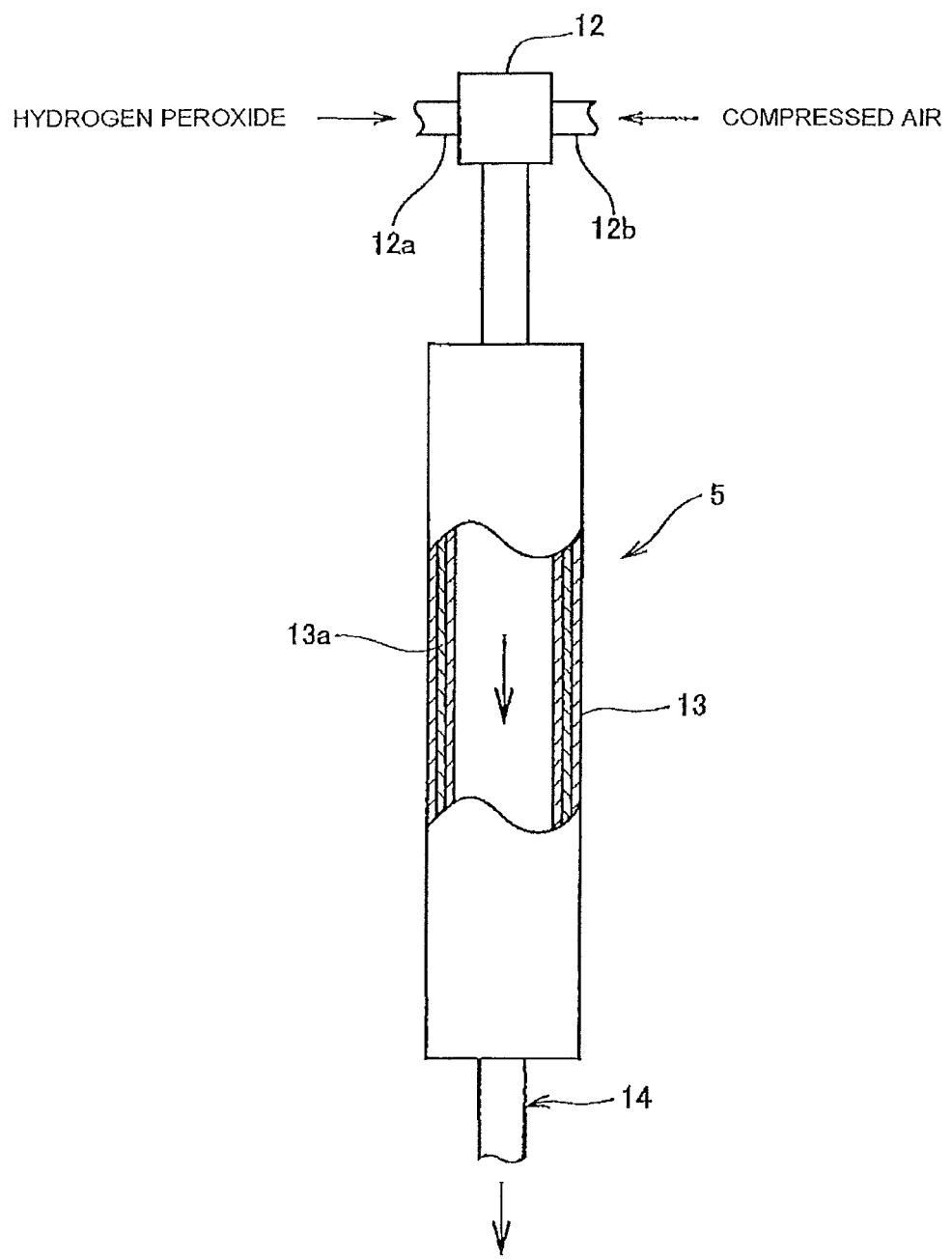
FIG. 6 shows a cross section of an apparatus that supplies hydrogen peroxide when sterilizing piping for compressed air according to the embodiment of the present invention.

FIG. 2 shows a circuit diagram showing a configuration for sterilizing the part of the inside of the air supply piping from the on-off valve 8 to the aseptic chamber 1. First, a sterilizer supply apparatus 5 supplies a sterilizer into the part of the inside of the air supply piping from the on-off valve 9 to the aseptic chamber 1. As shown in FIG. 6, the sterilizer supply apparatus 5 includes a sterilizer supplying portion 12 that is a twin-fluid spray nozzle for supplying the sterilizer in the form of liquid drops and an evaporating portion 13 for evaporating the sterilizer supplied from the sterilizer supplying portion 12 by heating the sterilizer to a temperature equal to or lower than the decomposition temperature thereof. The sterilizer supplying portion 12 is configured to take in the sterilizer from a sterilizer supply path 12a and compressed air from a compressed air supply path 12b and then sprays the sterilizer into the evaporating portion 13. The evaporating portion 13 is a pipe with a heater 13a interposed between inner and outer walls thereof, and the sterilizer blasted into the pipe is heated and evaporated. The evaporated sterilizer gas is jetted out of the evaporating portion 13 at a lower end of the evaporating portion 13. Instead of using the heater 13a, the evaporating portion 13 may be heated by dielectric heating.

A sterilizer blasting nozzle 14 is coupled to the lower end of the evaporating portion 13, and gas or mist of the sterilizer or a mixture thereof is blasted from the sterilizer blasting nozzle 14 into the part of the air supply piping to the aseptic chamber 1. The sterilizer blasted into the part of the air supply piping to the aseptic chamber 1 is in the form of gas or mist or a mixture thereof, because the sterilizer gasified in the evaporating portion 13 can be condensed into mist before the sterilizer is blasted from the sterilizer blasting nozzle 14.

Heated aseptic air may be supplied at a location between the lower end of the evaporating portion 13 and the sterilizer blasting nozzle 14, thereby mixing the heated aseptic air with the gas or mist of the sterilizer or a mixture thereof generated by the sterilizer supply apparatus 5.

With regard to operational conditions of the sterilizer supplying portion 12 of the sterilizer supply apparatus 5, the pressure of the compressed air is adjusted to fall within a range from 0.05 MPa to 0.6 MPa, for example. The sterilizer may be supplied by gravity or under pressure. The amount of the supplied sterilizer can be arbitrarily set. For example, the amount of the supplied sterilizer falls within a range from 1 g/min. to 100 g/min. The inner surface of the evaporating portion 13 is heated to 140° C. to 450° C. to evaporate the sprayed sterilizer.

The sterilizer preferably contains at least hydrogen peroxide. An appropriate content of hydrogen peroxide falls within a range from 0.5% by mass to 65% by mass. If the content is less than 0.5% by mass, the sterilizing power may be insufficient. If the content is more than 65% by mass, it is difficult to safely handle the sterilizer. Furthermore, a more preferable content is 0.5% by mass to 40% by mass. If the content is equal to or less than 40% by mass, the sterilizer can be more easily handled.

Although the sterilizer contains water, the sterilizer may contain one or more of alcohols such as methyl alcohol, ethyl alcohol, isopropyl alcohol, n-propyl alcohol and butyl alcohol, ketones such as acetone, methyl ethyl ketone and acetyl acetone, and glycol ethers, for example.

The sterilizer may further contain, as an additive agent, a compound having a sterilizing effect such as peracetic acid, acetic acid, a chlorine compound, sodium hydroxide, an alkaline compound such as potassium hydroxide, nitrous acid, ozone, or acid water, a cationic surface active agent, a non-ionic surface active agent, a phosphate compound, or the like.

After the sterilizer is supplied into the part of the air supply piping from the on-off valve 8 to the aseptic chamber 1, heated aseptic air or room-temperature aseptic air may be supplied into the air supply piping in order to remove the sterilizer remaining in the air supply piping and to increase the sterilization effect by heating the remaining sterilizer. The aseptic air may be supplied into the air supply piping from the air supply apparatus 2 through the sterilization filter unit 4 with the on-off valves 6, 8 and 10 open and the on-off valves 7, 9 and 11 closed.

After the sterilizer remaining in the part of the air supply piping from the on-off valve 8 to the aseptic chamber 1 is removed, aseptic air may be supplied into the air supply piping from the air supply apparatus 2 with the on-off valves 6 and 8 open and the on-off valves 7, 9, 10 and 11 closed as shown in FIG. 3, until operation of the aseptic filling machine is started. This is intended to maintain the aseptic condition of keep the interior of the air supply piping.

The air supply apparatus 2 is an air compressor, for example, and is driven by continuous or intermittent operation of a motor to supply air. The motor rotates to feed atmosphere into a tank of the air compressor, and the pressure in the tank increases. A pressure detection sensor is provided in the tank, and the motor stop rotating when the pressure in the tank reaches a preset upper limit value. The pressure in the tank decreases as the air is used, and when the pressure sensor detects a pressure equal to or lower than a preset lower limit value, the motor restarts, and the pressure in the tank increases. The pressure of the supplied air in this embodiment falls within a range from 0.01 MPa to 4.9 MPa. Low-pressure air is used for conveyance of caps or by an air blow gun used in the aseptic chamber of the aseptic filling machine, for example. High-pressure air is used as blow air for molding preforms into bottles in the aseptic filling machine. The air may be supplied with a blower, instead of the air compressor.

The air supplied by the air compressor contains dust, moisture, oil, organic chemical compounds or the like. A filter for removing these substances is preferably provided between the air supply apparatus 2 and the on-off valve 6. An air dryer for cooling the air supplied from the air supply apparatus 2 to condense moisture in the air is provided. The condensate is discharged through an automatic drain discharge valve provided in a lower part of the air dryer. Furthermore, a filter having pores having a diameter greater than 0.5 µm can be provided to remove dust and oil. Furthermore, a filter formed by fibers or grains of activated carbon may be provided to adsorb and remove organic chemical compounds into the activated carbon. Any impurities such as dust, moisture, oil or organic chemical compounds are preferably removed from the air before the air is supplied to the sterilization filter unit 4. If such impurities are removed by the sterilization filter unit 4, the service life of the sterilization filter unit 4 may be shortened.

Although the present invention is configured as described above, the present invention is not limited to the embodiment described above, and various modifications can be made without departing from the spirit and scope of the present invention.

REFERENCE SIGNS LIST 1 aseptic chamber
2 air supply apparatus
3 heated steam supply device
4 sterilization filter unit
5 sterilizer supply apparatus
S temperature sensor

The invention claimed is:

1. A method for sterilizing a sterilization filter unit, wherein heated steam is supplied to the sterilization filter unit, which sterilizes supplied air and discharged through an on-off valve, a temperature of the heated steam discharged from the sterilization filter unit is measured at predetermined time intervals, an F value is calculated from the measured temperature, and sterilization of the sterilization filter unit is ended when the F value reaches a target value, after sterilizing the sterilization filter unit, a part of an inside of an air supply piping from on-off valve located downstream the sterilization filter unit to an aseptic chamber is sterilized by supplying a sterilizer from a sterilizer supply apparatus with an on-off valve to supply the heated steam, the on-off valve located downstream the sterilization filter unit and the on-off valve to discharge the heated steam closed, and an on-off valve located upstream the chamber opened, after supplying the sterilizer, an aseptic air through the sterilization filter unit is supplied into the air supply piping in order to remove the sterilizer remaining in the air supply piping with an on-off valve to supply air to the sterilization filter unit and the on-off valve located downstream the sterilization filter unit opened, and an on-off valve to supply the sterilizer closed, and after removing the sterilizer remaining, the aseptic air is supplied into the air supply piping to maintain the aseptic condition of the interior of the air supply piping with the on-off valve located upstream the chamber closed.

2. The method for sterilizing a sterilization filter unit according to claim 1, wherein the F value is calculated according to the following formula:

$$F = \int_{t_0}^{t_1} 10^{(T-Tr)/Z} dt$$

wherein T is an optional sterilizing temperature (° C.), $10^{(T-Tr)/Z}$ is a fatality rate at the optional temperature T, Tr is a reference temperature (° C.), and Z is a Z value (° C.).

3. The method for sterilizing a sterilization filter unit according to claim 1, wherein the supplied air is air having a pressure equal to or higher than 0.1 MPa.

4. The method for sterilizing a sterilization filter unit according to claim 3, wherein the air is supplied to the sterilization filter unit after dust, oil or moisture is removed from the air.

* * * * *